(12) United States Patent
Leszko et al.

(10) Patent No.: US 9,895,232 B2
(45) Date of Patent: Feb. 20, 2018

(54) RELEASABLE THREADED CONNECTION FOR MODULAR IMPLANTS

(71) Applicant: DEPUY IRELAND UNLIMITED COMPANY, CO Cork OT (IE)

(72) Inventors: Filip Leszko, West Chester, PA (US);
Aaron Matyas, Fort Wayne, IN (US);
Kyle Steffe, Warsaw, IN (US); David E. Rottger, Kendallville, IN (US);
Daniel M. Hippensteel, Fort Wayne, IN (US)

(73) Assignee: DEPUY IRELAND UNLIMITED COMPANY, CO Cork (IE)

( * ) Notice: Subject to any disclaimer, the term of this patent is extended or adjusted under 35 U.S.C. 154(b) by 0 days.

(21) Appl. No.: 15/005,629

(22) Filed: Jan. 25, 2016

(65) Prior Publication Data

US 2017/0209277 A1    Jul. 27, 2017

(51) Int. Cl.
*A61F 2/38*        (2006.01)
*A61F 2/46*        (2006.01)
*A61F 2/30*        (2006.01)

(52) U.S. Cl.
CPC ............ *A61F 2/389* (2013.01); *A61F 2/3859* (2013.01); *A61F 2/461* (2013.01); *A61F 2002/30329* (2013.01); *A61F 2002/30405* (2013.01); *A61F 2002/30434* (2013.01); *A61F 2002/30507* (2013.01); *A61F 2002/3863* (2013.01); *A61F 2220/0041* (2013.01)

(58) Field of Classification Search
CPC combination set(s) only.
See application file for complete search history.

(56) References Cited

U.S. PATENT DOCUMENTS 5,984,970 A  * 11/1999  Bramlet ............ A61B 17/1659
                                              623/21.15
2009/0005876 A1* 1/2009  Dietz ................ A61B 5/0031
                                              623/20.36

* cited by examiner

*Primary Examiner* — Javier Blanco
(74) *Attorney, Agent, or Firm* — Barnes & Thornburg LLP

(57) ABSTRACT

An orthopedic prosthesis assembly includes a first prosthetic component, a second prosthetic component, and a fastener. The first prosthetic component includes a threaded bore. The second prosthetic component includes an opening and a threaded inner wall that extends inwardly from the opening. The fastener includes a first axial section having a first plurality of threads engaged with the threaded inner wall the second prosthetic component, and a second axial section having a second plurality of threads engaged with the threaded bore of the first prosthetic component to secure the first prosthetic component to the second prosthetic component.

3 Claims, 8 Drawing Sheets

RELEASABLE THREADED CONNECTION FOR MODULAR IMPLANTS

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a primary rosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

Such a primary knee prosthesis may also include a number of elongated intramedullary stem components and optional prosthetic components (e.g., sleeves and/or adaptors) which are implanted in the patient's tibia and/or femur. To secure a stem component and/or other components to the patient's tibia and/or femur, the intramedullary canal of the patient's tibia and/or femur is first surgically prepared (e.g., reamed) such that the stem component and/or other components may be subsequently implanted therein. In some designs, the stem component is implanted in the patient's bone by use of cementless fixation. One type of such a design is known as a 'press fit' stem component.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Various orthopaedic surgical instruments are used throughout such an orthopaedic procedure. For example, bone saws and/or reamers may be use to surgically prepare a bone surface to accept an orthopaedic implant. Additionally, depending on the particularly implant, a variety of orthopaedic surgical instruments may be used to assembly, disassembly, and/or install the orthopaedic implant into the prepared bone.

SUMMARY

According to one aspect of the disclosure, an orthopaedic surgical instrument is disclosed. The orthopaedic surgical instrument includes a first prosthetic component, a second prosthetic component, and a fastener. The first prosthetic component includes a first end, a second end opposite the first end, and a threaded bore defined in the first end. The second prosthetic component includes an outer surface, an inner surface positioned opposite the outer surface that is configured to face a bone of a patient, and a post extending from the inner surface along a longitudinal axis, the post including an opening defined in a free end and a threaded inner wall that extends inwardly from the opening to define a lower passageway in the post. The fastener includes a first axial section having a first plurality of threads engaged with the threaded inner wall the second prosthetic component, and a second axial section having a second plurality of threads engaged with the threaded bore of the first prosthetic component to secure the first prosthetic component to the first prosthetic component.

In some embodiments, the first plurality of threads and the second plurality of threads twist in opposite directions.

In some embodiments, the first plurality of threads are one of right-handed threads and left-handed threads and the second plurality of threads are the other of right-handed threads and left-handed threads.

In some embodiments, the first plurality of threads twist in a same direction as the second plurality of threads.

In some embodiments, the first plurality of threads and the second plurality of threads are one of right-handed threads and left-handed threads.

In some embodiments, the first plurality of threads has a first thread pitch and a first lead and the second plurality of threads has a second thread pitch that is same as the first thread pitch and a second lead that is the same as the first thread pitch.

In some embodiments, the outer surface of the second prosthetic component has an opening defined therein, and an upper passageway connects the opening to the lower passageway.

In some embodiments, the orthopaedic prosthesis system further includes a tool having an end sized to be received in the upper passageway and is configured to engage the head of the fastener to selectively rotate the fastener and decouple the first prosthetic component from the second prosthetic component.

In some embodiments, the rotation of the fastener in a first direction causes the fastener to move axially away from the second prosthetic component within the upper passageway of the component.

In some embodiments, the first prosthetic component is a stem component having an elongated body extending from the first end, and the second prosthetic component is a femoral component having a pair of condyle surfaces.

In some embodiments, the first prosthetic component is a stem component having an elongated body extending from the first end, and the second prosthetic component is a tibial component comprising a tibial tray having a platform and the post extends from the platform.

According to another aspect of the disclosure, a method for joint line assembly of an orthopaedic prosthesis assembly is disclosed. The method includes threading a first axial section of a fastener into a threaded bore defined in a first prosthetic component by rotating the fastener in a first direction, and threading a second axial section of the fastener into a threaded lower passageway defined in a second prosthetic component by rotating the first prosthetic component in a second direction to secure the first prosthetic component to the second prosthetic component.

In some embodiments, the method further includes advancing a tool through an upper passageway defined in the second prosthetic component to engage an end of the tool to the second axial section of the fastener, and rotating the tool in the second direction with the end of the tool engaged with the fastener to move the first axial section of the fastener out of engagement with the first prosthetic component.

In some embodiments, the first axial section includes a first plurality of threads having a first thread pitch and the second axial section includes a second plurality of threads having a second thread pitch that matches the first thread pitch.

In some embodiments, the second axial section has a diameter greater than a diameter of the first axial section of the fastener.

According to another aspect of the disclosure, another method includes engaging a first axial section of a fastener with a threaded bore defined in a first prosthetic component, engaging a second axial section of the fastener into a threaded lower passageway defined in a second prosthetic component, and rotating the fastener in a first direction to simultaneously move the first axial section and the second axial section into the first prosthetic component and the second prosthetic component, respectively.

In some embodiments, the method further includes advancing a tool through an upper passageway defined in the second prosthetic component extending away from the lower passageway, engaging an end of the tool to the second axial section of the fastener, and rotating the tool in a second direction to simultaneously move the first axial section and the second axial section out of engagement with the first prosthetic component and the second prosthetic component, respectively.

In some embodiments, the first axial section has a same diameter as a diameter of the second axial section.

BRIEF DESCRIPTION OF THE DRAWINGS

The detailed description particularly refers to the following figures, in which.

DETAILED DESCRIPTION OF THE DRAWINGS

Figure 1:
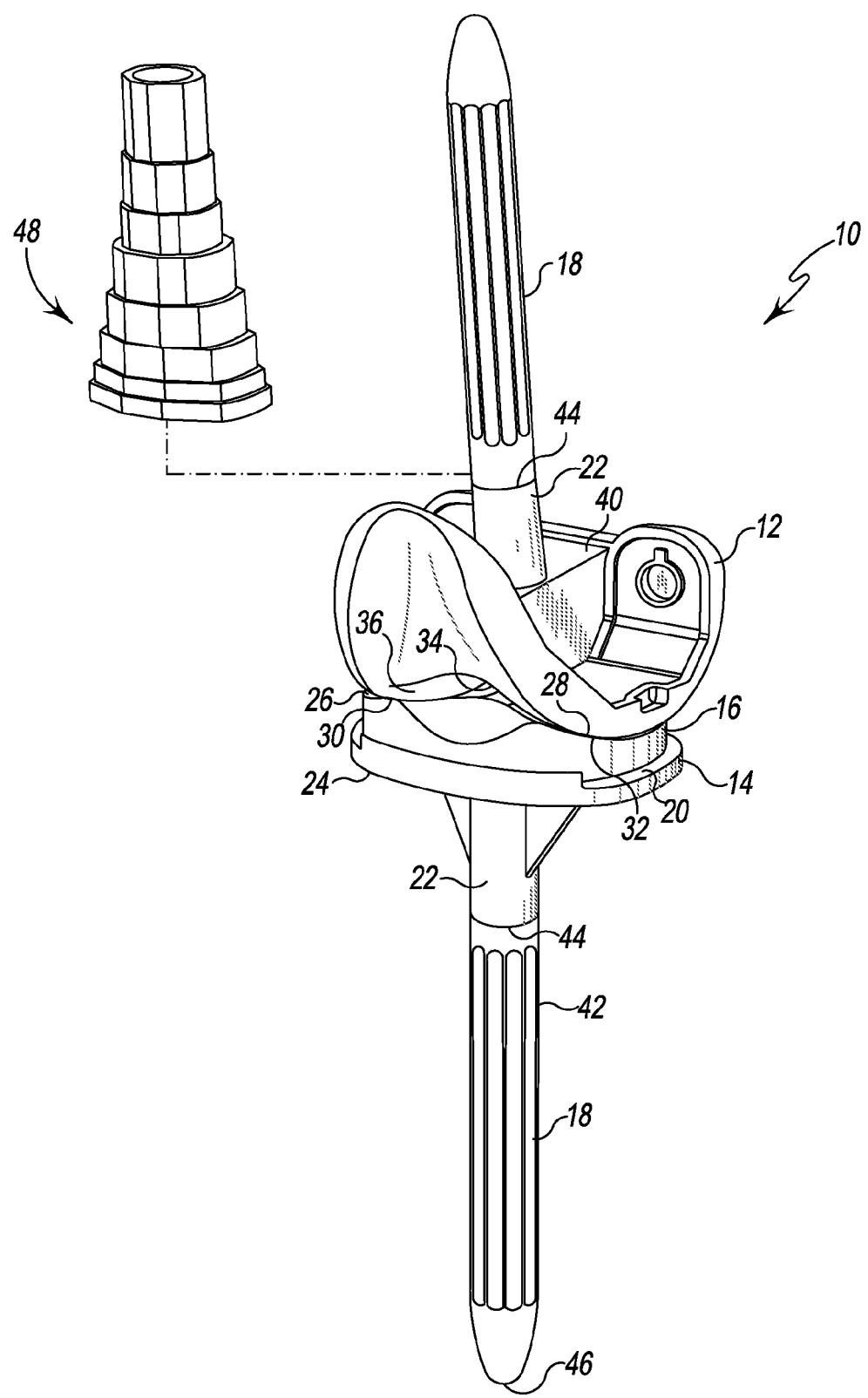
FIG. 1 is a perspective view of an implantable orthopaedic knee prosthesis assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring to FIG. 1, an implantable orthopaedic knee prosthesis assembly 10 for use in the performance of an orthopaedic knee replacement procedure is shown. The knee prosthesis assembly 10 includes a femoral component 12, a tibial tray component 14, and a bearing 16. The knee prosthesis assembly 10 also includes a stem component 18 secured to the femoral component 12 and a stem component 18 secured to the tibial tray component 14. As will be described in detail below, each of the components 12, 14 is secured to the stem component 18 via a fastener such that the selected component 12, 14 may be disassembled and removed separately from the stem component 18 while the components 12, 14, 18 are positioned in the patient's bone.

The tibial tray component 14 is configured to be implanted into a surgically-prepared proximal end of a patient's tibia (not shown). The tibial tray component 14 includes a platform 20 having an elongated stem mounting post 22 extending inferiorly away from its inferior surface 24. The mounting post 22 is configured to engage the stem component 18, as will be described in more detail below.

The bearing 16 is securable to the tibial tray component 14. In particular, the bearing 16 may be snap-fitted into the tibial tray component 14 such that the bearing 16 is fixed relative to the tibial tray component 14 (i.e., it is not rotatable or moveable in the anterior/posterior or medial/lateral directions). In other embodiments, the bearing 16 may be secured in a manner that allows it to rotate relative to the tibial tray component 14. The bearing 16 includes a lateral bearing surface 26 and a medial bearing surface 28. The bearing surfaces 26, 28 are configured to articulate with a lateral condyle surface 30 and a medial condyle surface 32, respectively, of the femoral component 12. Specifically, the femoral component 12 is configured to be implanted into a surgically-prepared distal end of a patient's femur, and is configured to emulate the configuration of the patient's natural femoral condyles. As such, the lateral condyle surface 30 and the medial condyle surface 32 are configured (e.g., curved) in a manner which mimics the condyles of the natural femur. The lateral condyle surface 30 and the medial condyle surface 32 are spaced apart from one another thereby defining an intercondylar notch 34 therebetween.

The condyle surfaces 30, 32 are formed in a bearing surface 36 of the femoral component 12. The femoral component 12 also includes an elongated stem mounting post 22, extending superiorly away from its opposite backside surface 40, which is configured to engage the stem component 18, as will be described in more detail below. The stem component 18 and the femoral component 12 may be implanted into a surgically-prepared (e.g., reamed or broached) patient's femur (not shown).

As shown in FIG. 1, each of the stem components 18 includes an elongated, generally cylindrical stem body 42. The elongated stem body 42 further includes a threaded bore 120 defined at an end 44 thereof (see FIGS. 3-13). When the stem component 18 is secured to the tibial tray component 14, the end 44 is the proximal end of the elongated stem body 42, which extends distally away from the post 22 of the tray component 14 and terminates at rounded distal end 46 that defines the inferior-most surface of the stem component 18. When the stem component 18 is secured to the femoral component 12, the end 44 is the distal end of the elongated stem body 42, which extends proximally away from the mounting post 22 of the femoral component 12 and terminates at rounded proximal end 52 that defines the superior-most surface of the stem component 18.

The stem component 18 may be provided in a number of different configurations in order to fit the needs of a given patient's anatomy. In particular, the stem component 18 may be configured in various different lengths to conform to the patient's anatomy (e.g., a relatively long stem component 18 for use with a long femur or tibia, a relatively short stem component 18 for use with a short femur or tibia, etcetera). The stem component 18 may also be provided in varying body diameters to fit the needs of a given patient's anatomy. The body diameter of a given stem component 18 is the stem component's medial/lateral cross sectional width in the cylindrical midsection of the stem component's body (i.e., not at its tapered post or its distal tip). In other embodiments, the stem component 18 may have some other shape (e.g., non-cylindrical) and size. Likewise, the femoral component 12 and the tibial tray component 14 may be provided in various different sizes to fit the needs of a given patient's anatomy.

The knee prosthesis assembly 10 may also include a number of optional components in various embodiments. For example, the knee prosthesis assembly 10 may include a femoral sleeve component 48. The femoral sleeve component 48 may be used to facilitate implantation of the femoral component 12 in the presence of reduced bone quality in the patient's femur. The femoral sleeve component 48 is configured to be secured to the femoral component 12 so as to be positioned between the femoral component 12 and the stem component 18.

Figure 2:
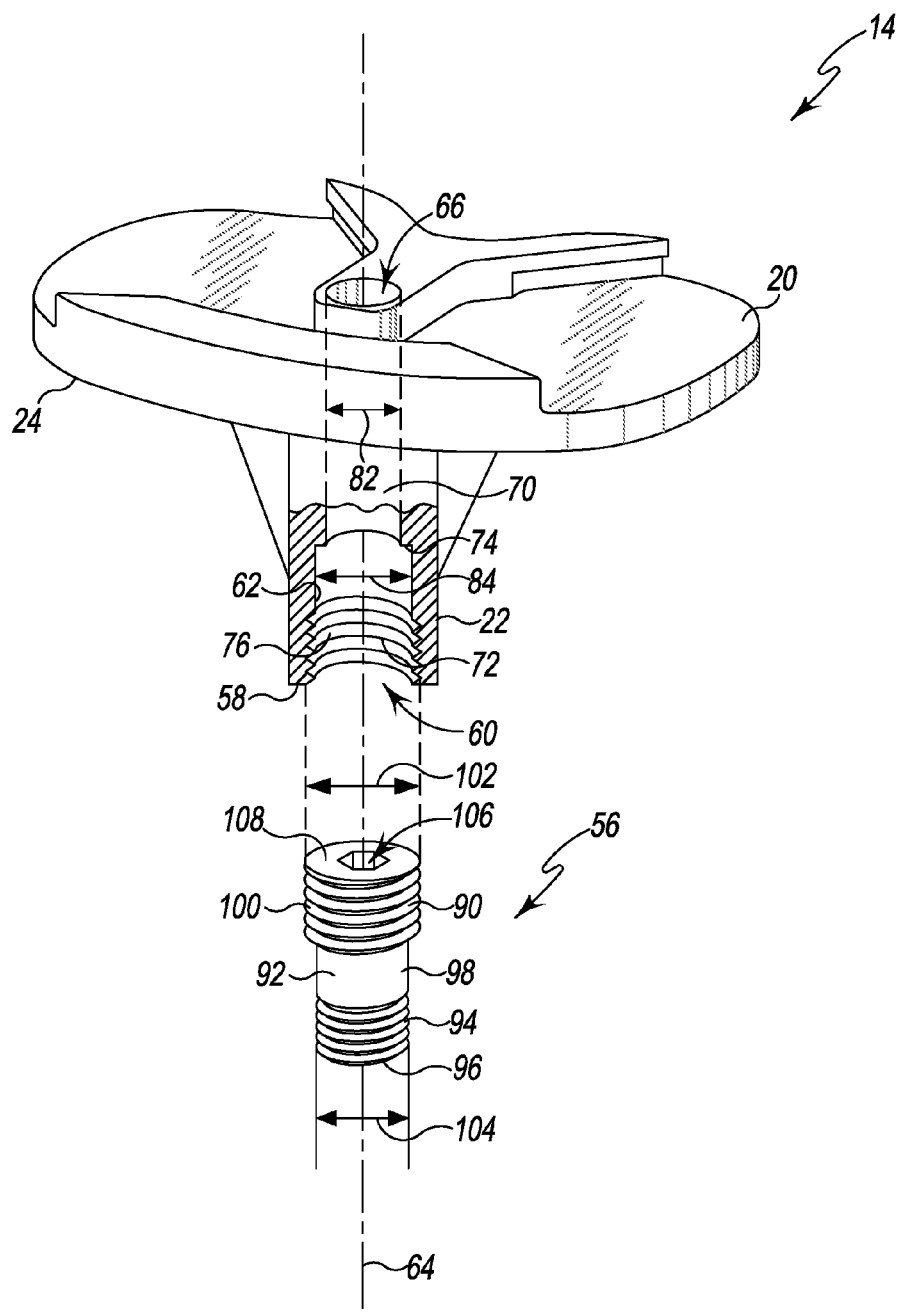
FIG. 2 is an exploded, partial cross-section perspective view of a tibial tray component and a fastener of the implantable orthopaedic knee prosthesis assembly of FIG. 1.

Referring now to FIG. 2, the tibial tray component 14 is shown with a fastener 56 that is configured to attach the tibial tray component 14 to the stem component 18. As described above, the tibial tray component 14 includes the platform 20 having the mounting post 22 extending inferiorly away from the inferior surface 24 of the platform 20 to an outer end 58. The mounting post 22 further includes an outer opening 60 defined in the outer end 58 and an inner wall 62 that extends inwardly from the outer opening 60 along the longitudinal axis 64 to a proximal opening 66 defined the platform 20 of the tibial tray component 14. The inner wall 62 of the tibial tray component 14 defines a first passageway 70 and a second passageway 72. A rim surface 74 of the inner wall 62 is defined at the intersection of the first passageway 70 and the second passageway 72.

The first passageway 70 extends away from the proximal opening 66 of the platform 20 to the rim surface 74 of the mounting post 22. The second passageway 72 extends inferiorly from the rim surface 74 to the outer opening 60 at the outer end 58 of the mounting post 22. The inner wall 62 includes a plurality of internal threads 76 in the second passageway 72 that are configured to receive corresponding threads of the fastener 56. Further, the passageway 70 has a diameter 82 smaller than a diameter 84 of the passageway 72 such that the rim surface 74 is defined between the inner ends of the passageways 70, 72, as shown in FIG. 2. The passageway 72 is configured to receive the fastener 56 and the passageway 70 is configured to receive a surgical instrument tool 150, as will be described in more detail below.

As shown in FIG. 2, the fastener 56 is embodied as a screw. It should be appreciated, however, that the fastener 56 may be any fastening device or component configured to extend through the tibial tray component 14 to the stem component 18 to secure the tibial tray component 14 to the stem component 18. The fastener 56 includes an elongated shaft 92 having a threaded first section 90 and a threaded second section 94 positioned opposite the first section 90. A substantially smooth unthreaded section connects the sections 90, 94. It should be appreciated that in other embodiments the entire shaft of the fastener may be threaded.

Figure 4:
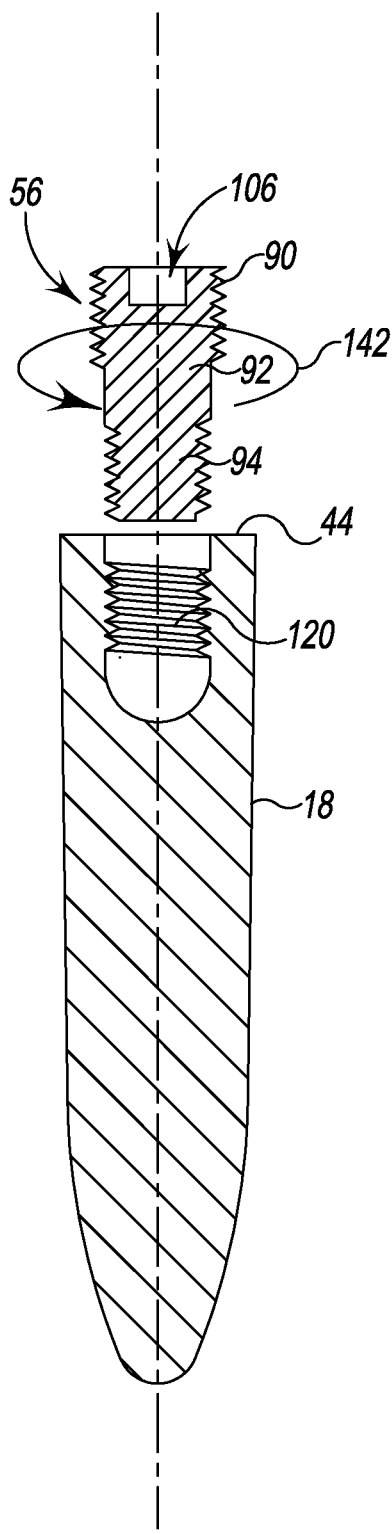
FIGS. 4-5 are cross sectional elevation views showing the fastener being attached to the stem component of FIG. 1.
Figure 5:
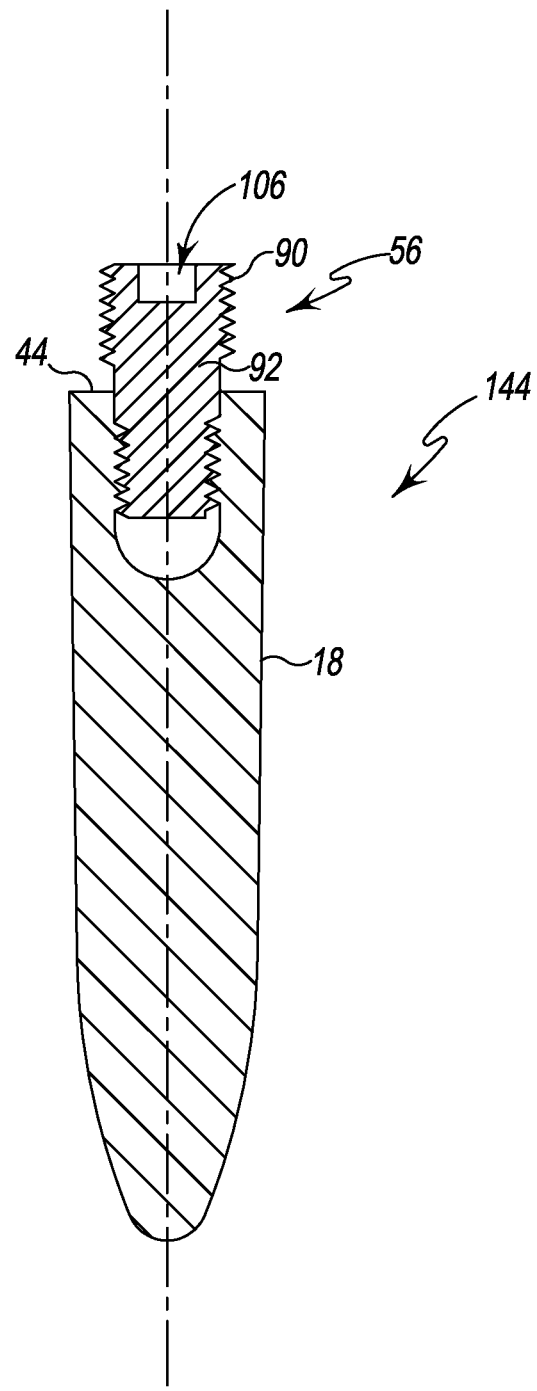
Figures 6, 7:
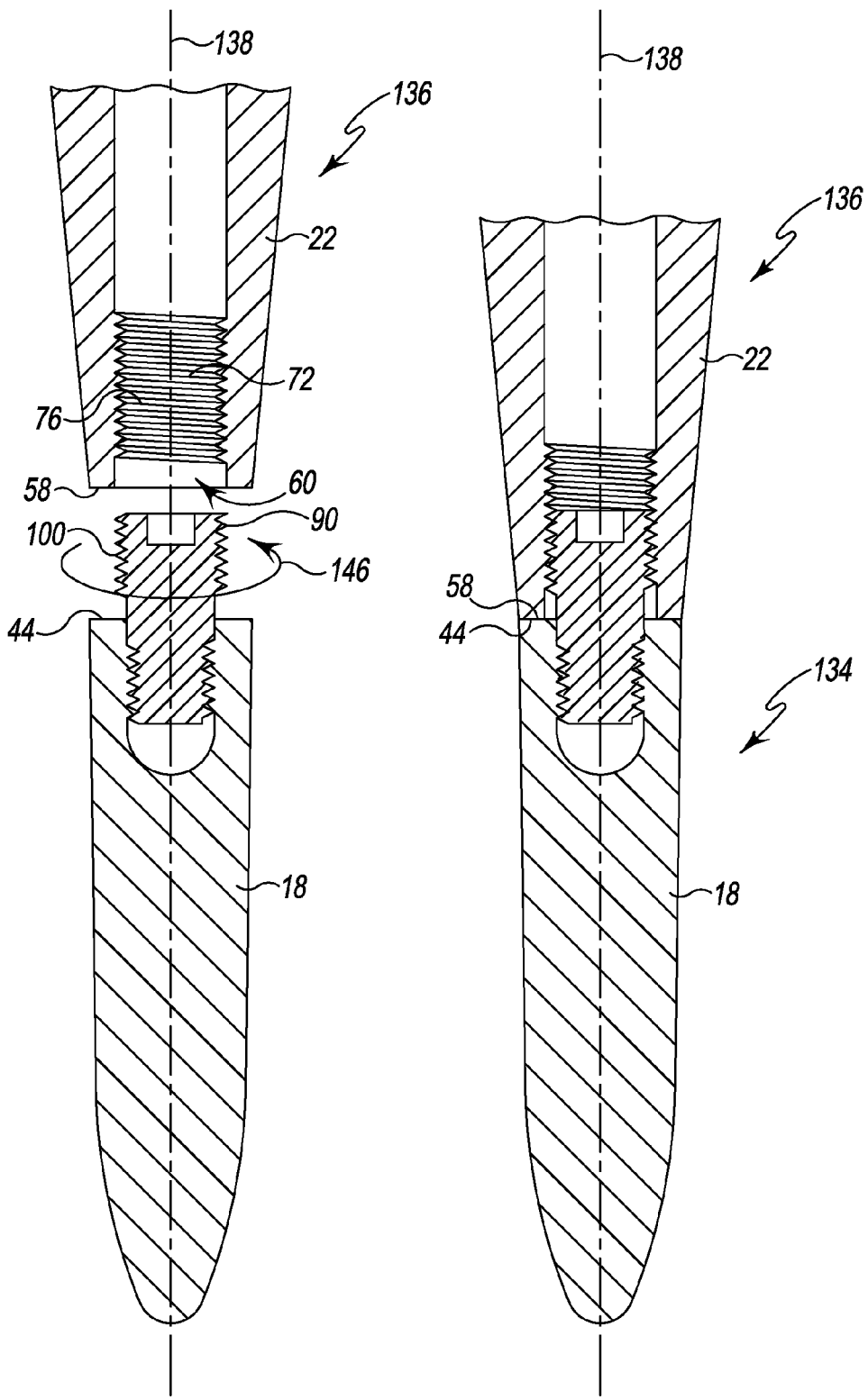
FIGS. 6-7 are cross sectional elevation views showing a procedure for attaching a prosthetic component to the stem component and fastener to form a component assembly.

The threads of the section 90 twist in the same direction as the threads of the section 94. Specifically, in the illustrative embodiment, the section 94 has right-handed threads 98 and the section 90 has right-handed threads 100. As a result, when the fastener 56 is rotated in one direction, it is advanced in the same direction relative to either the stem component 18 or the tibial tray component 14. For example, when the fastener 56 is rotated clockwise relative to the stem component 18, it may be threaded into the threaded bore 120 of the stem component 18, as shown in FIGS. 4-5. When the fastener 56 is rotated counterclockwise, as shown in FIGS. 6-7, it may be advanced out of the stem component 18 and into the tibial tray component 14. In the illustrative embodiment, the thread pitch and lead of the section 90 matches the thread pitch and lead of the section 94 so that one rotation of the fastener 56 in either direction results in the same travel axially for the sections 90, 94.

Further, the section 90 has a diameter 102 greater than a diameter 82 of the first passageway 70 of the tibial tray component 14 and a diameter 104 of the fastener section 94. Accordingly, the section 90 of the fastener 56 may be positioned in the second passageway 72 of the tibial tray component 14 but does not pass beyond the rim surface 74 into the first passageway 70. In some embodiments, the second passageway 72 may include a relatively smooth upper section and a threaded lower section. In such embodiments, the fastener 56 may be threaded through the threaded lower section of the lower passageway but does not advance beyond the lower threaded section.

As shown in FIG. 2, the shaft 92 of the fastener 56 further includes a tool socket 106 defined in an upper surface 108. The tool socket 106 is shaped to accept a surgical instrument tool 150, as will be described in detail below.

Figure 3:
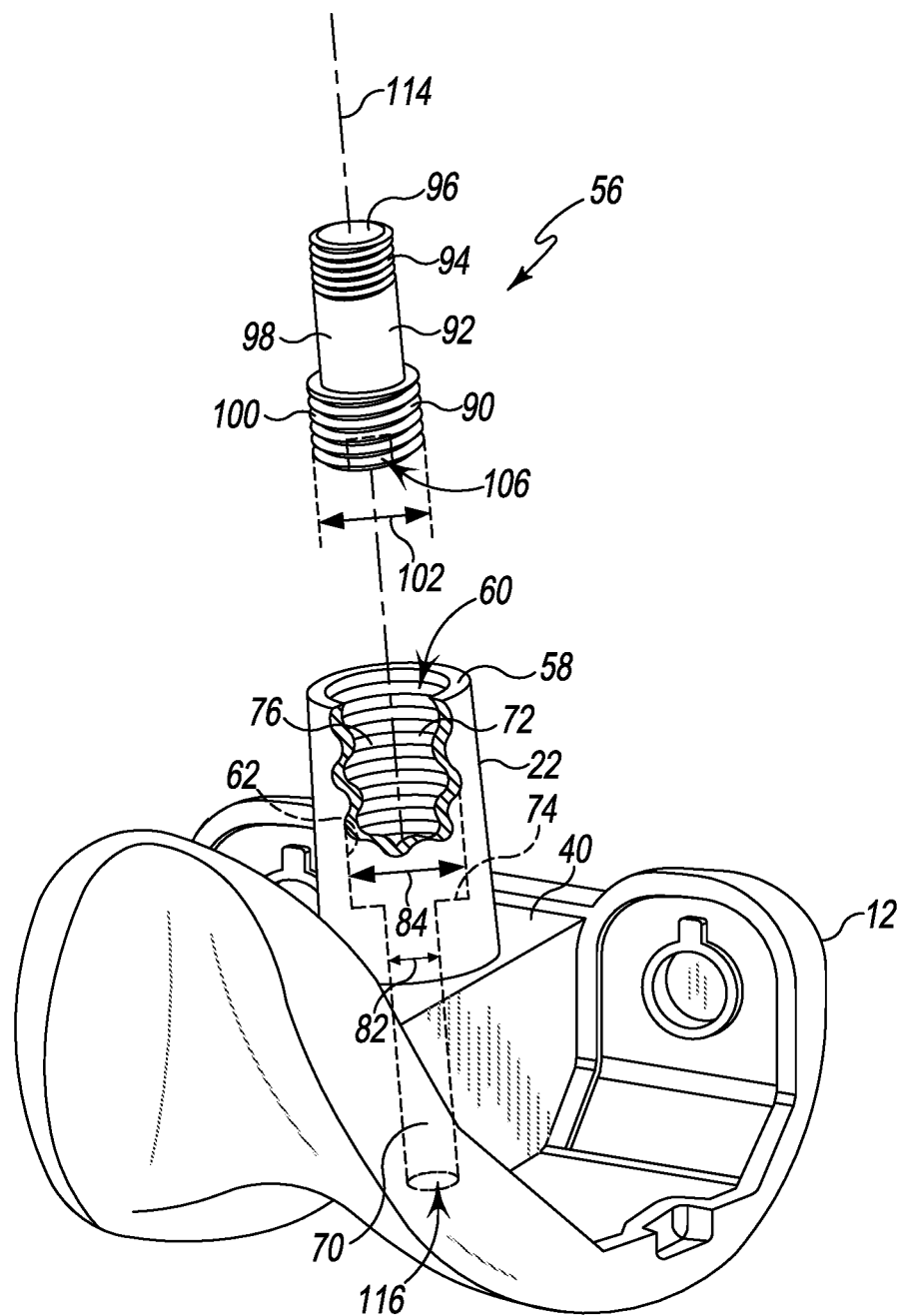
FIG. 3 is an exploded, partial cross-section perspective view of a femoral component and the fastener of the implantable orthopaedic knee prosthesis assembly of FIG. 1.

Referring now to FIG. 3, the femoral component 12 also includes a mounting post 22 that extends superiorly away from its opposite backside surface 40. The mounting post 22 of the femoral component 12 also includes an outer end 58 and an inner wall 62 that extends inwardly from an opening 60 along the longitudinal axis 114 to a distal opening 116 defined in the intercondylar notch 34 of the femoral tray component 12. The inner wall 62 of the femoral tray component 12 defines a first passageway 70 and a second passageway 72 in the post 22. A rim surface 74 of the inner wall 62 is defined at the intersection of the first passageway 70 and the second passageway 72.

The first passageway 70 extends away from the distal opening 116 to the rim surface 74 of the mounting post 22 of the femoral component 12. The second passageway 72 extends away from the rim surface 74 to the outer opening 60 at the outer end 58 of the mounting post 22. The inner wall 62 includes a plurality of internal threads 76 in the second passageway 72 that are configured to receive corresponding threads of the fastener 56. Further, the passageway 70 has a diameter 82 smaller than a diameter 84 of the passageway 72 such that the rim surface 74 is defined between the inner ends of the passageways 70, 72, as shown in FIG. 3. The passageway 72 is configured to receive the fastener 56 and the passageway 70 is configured to receive a surgical instrument tool 150

As described above, the fastener 56 includes an elongated shaft 92 having a threaded first section 90 and a threaded second section 94 positioned opposite the first section 90. Because the fastener section 90 has a diameter 102 greater than a diameter 82 of the first passageway 70 of the femoral component 12, the section 90 of the fastener 56 may be positioned in the second passageway 72 of the femoral component 12 but does not pass beyond the rim surface 74 into the first passageway 70.

Referring now to FIGS. 4-7, a procedure for assembling a component assembly 134 is shown. The component assembly 134 may include a selected prosthetic component 136 such as, for example, a femoral component 12 or tibial tray component 14, and a stem component 18. To prepare the component assembly 134, the surgeon may first align the elongated shaft 92 of the fastener 56 to the threaded bore 120 of the stem component 18, as shown in FIG. 4. The surgeon may then rotate the fastener 56 in the direction indicated by arrow 142 such that the threaded section 94 of the elongated fastener shaft 92 may advance axially into the threaded bore 120 of the stem component 18, thereby forming an intermediate assembly 144, as shown in FIG. 5. In the illustrative embodiment, the direction of arrow 142 is clockwise because the threads 98 of the fastener section 94 are right-handed threads. In other embodiments, the threads may twist in the opposite direction (i.e., may be left-handed threads).

The intermediate assembly 144 may then be attached to the selected prosthetic component 136 to form the component assembly 134 as shown in FIGS. 6-7. In the illustrative embodiment, the surgeon may thread the threaded section 90 of the fastener 56 into the threaded passageway 72 of the selected component 136 by rotating the entire intermediate assembly 144 counterclockwise, as indicated by arrow 146. For example, if the selected component 136 is a tibial tray component 14, the surgeon may align the threaded section 90 of the fastener 56 with the passageway 72 of the mounting post 22 of the tibial tray component 14. The surgeon may then rotate the intermediate assembly 144 in the direction indicated by arrow 146 (i.e., counterclockwise), which is opposite the first direction 142 (i.e., clockwise). As the threaded section 90 of the fastener 56 of the intermediate assembly 144 is rotated into the outer opening 60 of the mounting post 22, the external threads 100 of the threaded section 90 are threaded superiorly into the internal threads 76 of the passageway 72. The user may continue to rotate the intermediate assembly 144 to move the end 44 of the stem component 18 into contact with the outer end 58 of the mounting post 22. When the stem component 18 contacts the mounting post 22, the threaded section 90 is fully positioned in the second passageway 72 of the mounting post 22, and the prosthetic component 136 (i.e., the tibial tray component 14 or femoral component 12) is securely coupled to the stem component 18 via the fastener 56, thereby forming a component assembly 134, as shown in FIG. 7. The assembly 134 may then be impacted in a surgically-prepared patient's bone.

Figure 8:
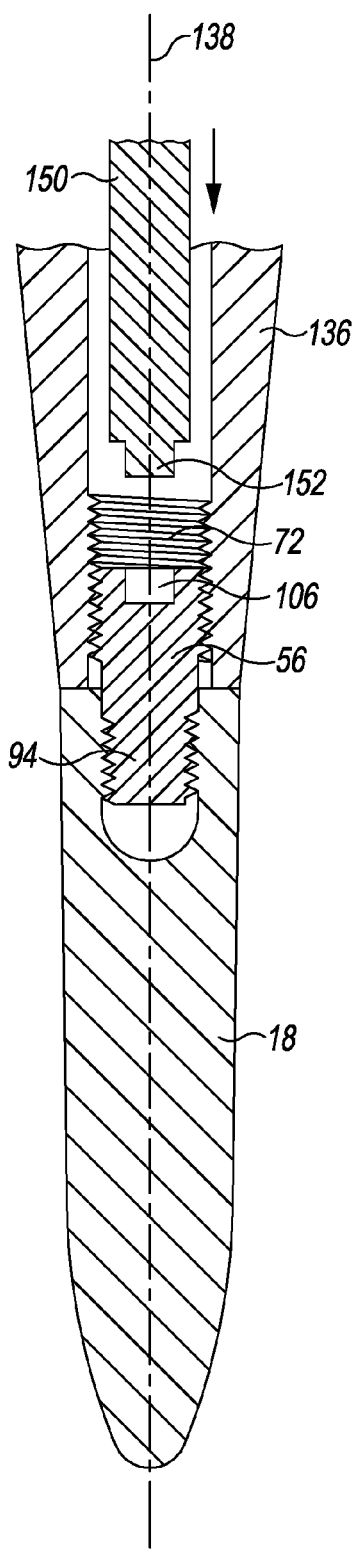
FIGS. 8-10 are cross sectional elevation views showing a surgical tool being used to remove the fastener from the stem component to disassemble the component assembly of FIGS. 6-7.
Figure 9:
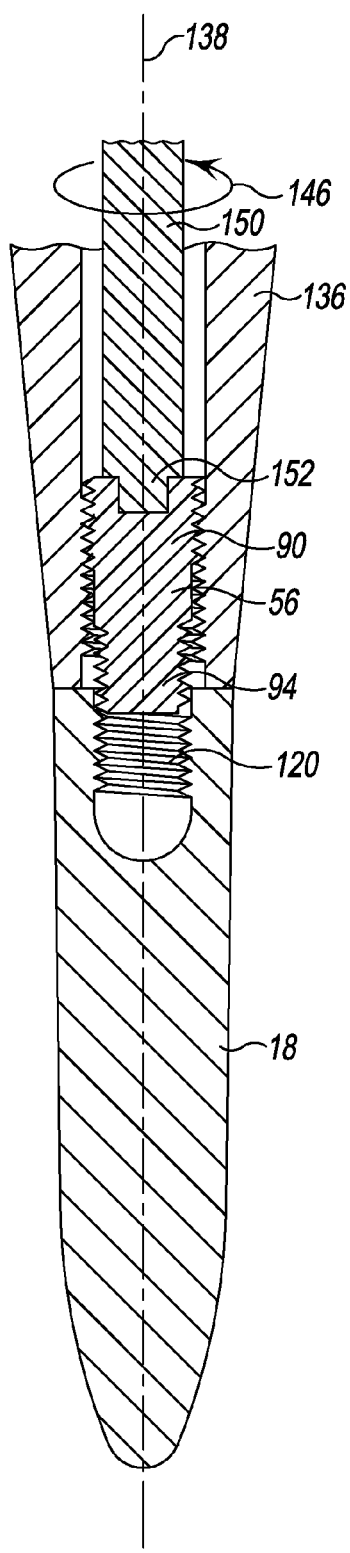
Figure 10:
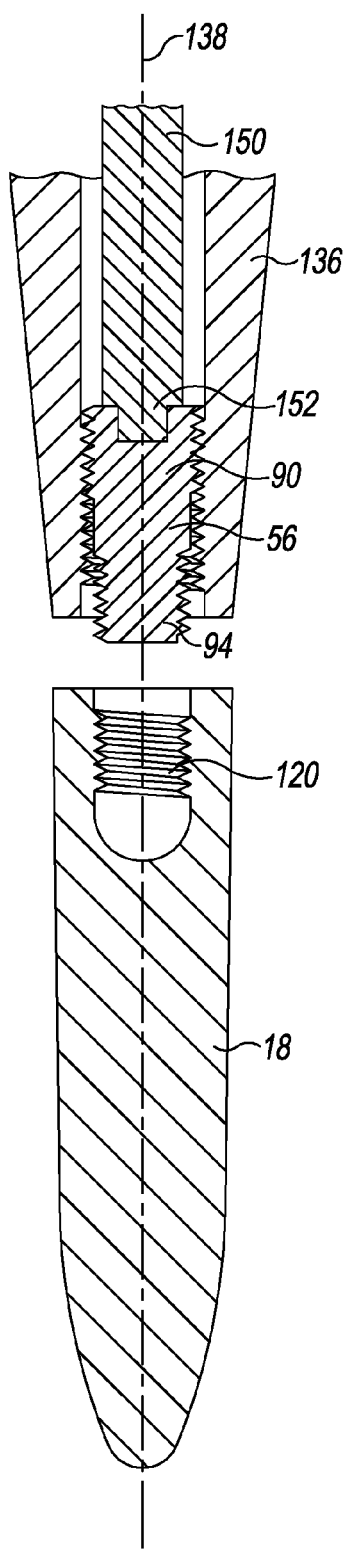

Referring now to FIGS. 8-10, should a revision surgery become necessary, the surgeon may disassemble the component assembly 134 to remove the assembly 134 from the patient's bone. To do so, the surgeon may remove the selected component independently from the stem component 18 positioned in the patient's intramedullary canal. In the illustrative embodiment, removing the selected component from the stem component 18 involves unscrewing the fastener 56 from the stem component 18 to move the threaded section 94 of the fastener 56 completely out of engagement with the threaded bore 120 of the stem component 18. As described previously, the threaded section 90 of the fastener 56 includes the tool socket 106 that is shaped to accept a surgical instrument tool 150. For example, the tool socket 106 may be hex-shaped to accept a hex driver. The tool socket 106 may be otherwise shaped to accept a surgical instrument tool head 152 of a different shape.

For example, FIGS. 8-10 illustrate the disassembly process of the component assembly 134 when the selected component 136 is the tibial tray component 14. To remove the tibial tray component 14 from the stem component 18, the surgeon may advance the tool head 152 of the tool 150 through the proximal opening 66 into the first passageway 70 of the component 14 and into the tool socket 106 of the fastener 56. The surgeon may then rotate the surgical instrument tool 150 to move the threaded section 94 of the fastener 56 out of engagement with the threaded bore 120 of the stem component 18. When the tool head 152 is properly inserted into the tool socket 106 of the fastener 56, the surgeon may rotate the surgical instrument tool 150 about the longitudinal axis 138 in the second direction 146 (i.e., counterclockwise). As the tool 150 rotates the fastener 56 in the second direction 146, the threaded section 90 of the fastener 56 moves axially out of the stem component 18 and deeper into the passageway 72 of the tibial tray component 14.

As described previously, the section 94 of the fastener 56 has the diameter 104 smaller than the diameter 102 of the section 90 of the fastener 56. Accordingly, as the section 90 advances axially, the section 94 also advances into the passageway 72 of the tibial tray component 14, as shown in FIG. 9, until the fastener 56 is completely disengaged from the threads of the stem component 18, as shown in FIG. 9. When the elongated shaft 92 is positioned fully in the lower passageway 72, the threaded section 94 of the fastener 56 does not engage the internal threads 76 of the second passageway 72 of the tibial tray component 14. The surgeon may then remove the tibial tray component 14 from the patient's bone while the stem component 18 remains in the intramedullary canal. Subsequently, the stem component 18 may be removed from the intramedullary canal of the patient's tibia using another removal tool. The surgeon may then assemble a revision component assembly including another tibial tray component and stem component and may implant the revision component assembly 134 back into the intramedullary canal of the patient's tibia.

Referring now to FIGS. 11-14, a component assembly 234 is shown with another embodiment of a fastener (hereinafter fastener 256). The embodiment of FIGS. 11-14 includes many of the same features described above in regard to FIGS. 1-10. The same reference numbers are used in FIGS. 11-14 to identify features that are the same or similar to those described above in regard to FIGS. 1-10. In the illustrative embodiment, the component assembly 234 may include a selected prosthetic component 136 such as, for example, a femoral component 12 or tibial tray component 14, and a stem component 218. Similar to the stem component 18 described above, the stem component 218 includes an elongated stem body 42 that has a threaded bore 220 defined at an end 44 thereof. In the embodiment of FIGS. 11-14, the elongated body 42 has a plurality of left-handed threads 240 that define the bore 220.

Figure 11:
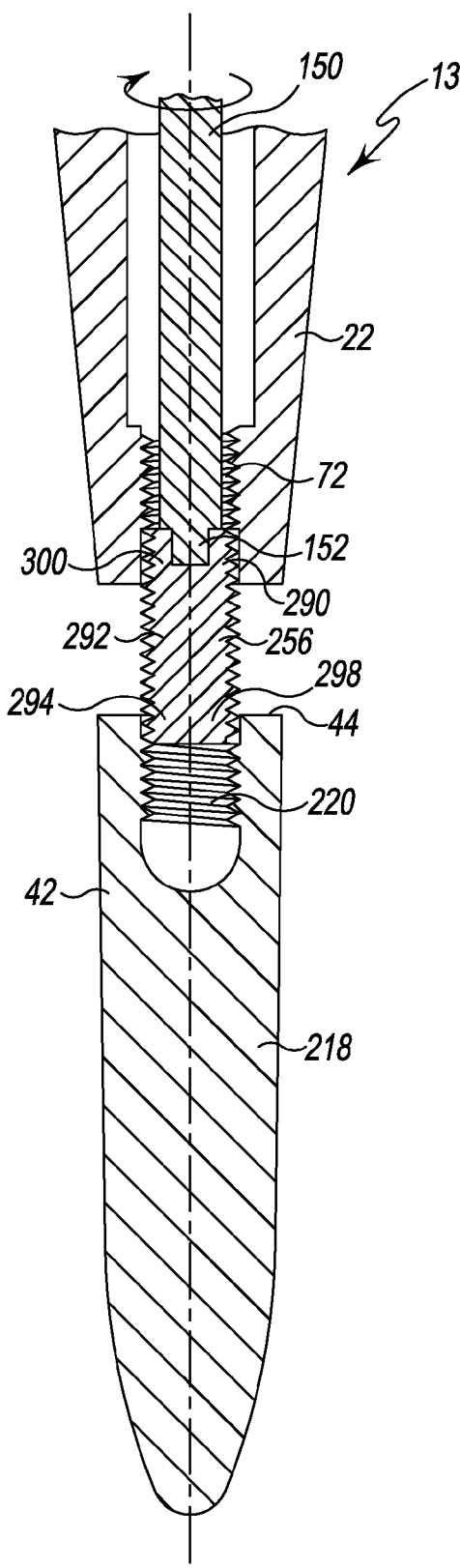
FIGS. 11-12 are cross sectional elevation views showing another embodiment of the fastener being used to attach a prosthetic component to the stem component to form an component assembly.

As shown in FIG. 11, the fastener 256 is embodied as a screw. It should be appreciated, however, that the fastener 256 may be any fastening device or component configured to extend through the component 136 to the stem component 218 to secure the component 136 (i.e., the tibial tray component 14 or the femoral component 12) to the stem component 18. The fastener 256 includes an elongated shaft 292 having a threaded first section 290 and a threaded second section 294 positioned opposite the first section 290. A substantially smooth unthreaded section connects the sections 290, 294. It should be appreciated that in other embodiments the entire shaft of the fastener may be threaded.

The threads of the section 290 twist in one direction and the threads of the section 294 twist in the opposite direction. Specifically, in the illustrative embodiment, the section 294 has left-handed threads 298 and the section 290 has right-handed threads 300. Accordingly, when the fastener 256 is rotated counterclockwise or clockwise, it is advanced in opposite directions relative to the stem component 218 and the component 236.

Figure 12:
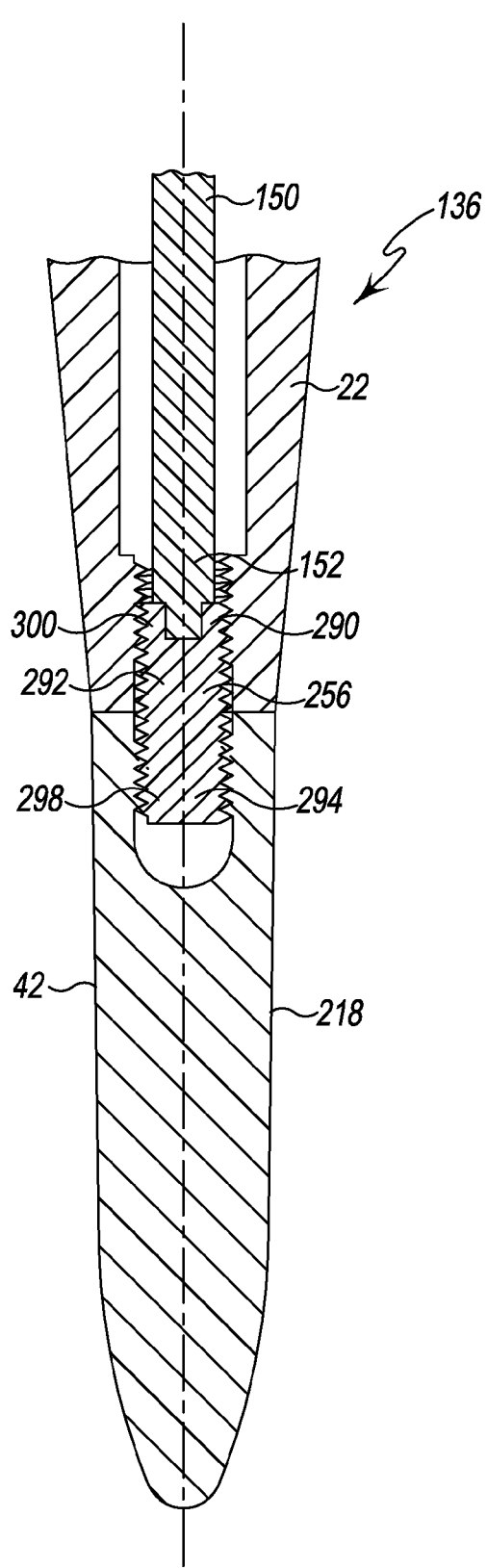

For example, as shown in FIGS. 11-12, the fastener 256 may be aligned with both the mounting post 22 of the component 136 and the threaded bore 220 of the stem component 218. When the fastener 256 is rotated counterclockwise, it may be threaded in one direction deeper into the threaded bore 220 of the stem component 218 and in the opposite direction deeper into the mounting post 22 of the component 136. As a result, the fastener 256 is rotated in only a single direction to assemble the component 236 with the stem component 218.

Figures 13, 14:
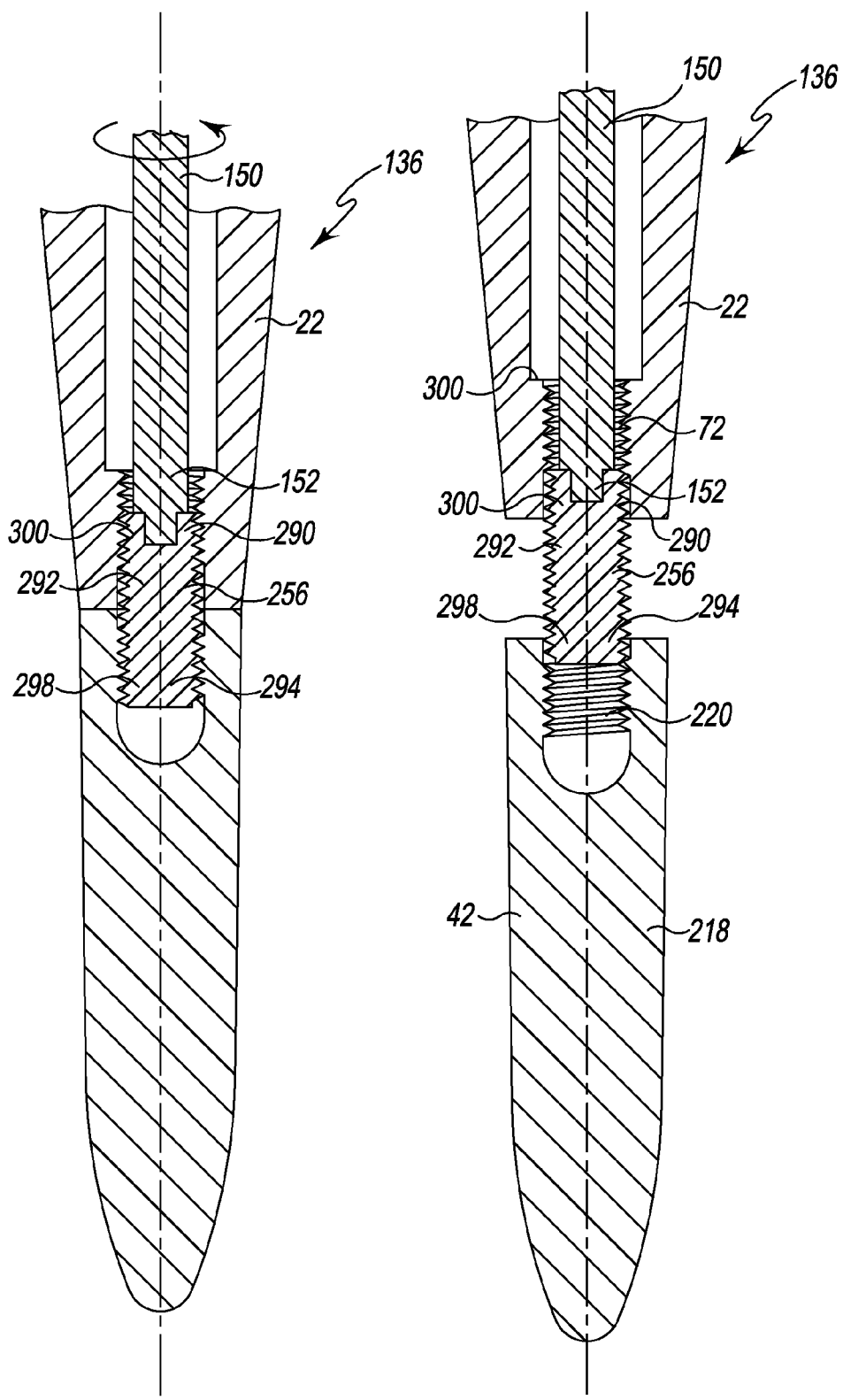
FIGS. 13-14 are cross sectional elevation views showing a procedure for disassembling the component assembly of FIGS. 11-12.

As shown in FIGS. 12-13, when the fastener 256 is rotated clockwise, it may be drawn in one direction, out of the threaded bore 220, and it may be drawn in the other direction, out of the mounting post 22 of the component 135. In that way, the fastener 256 is rotated in only a single direction to dissemble the component 236 from the stem component 218. As with the fastener 56, the shaft 292 of the fastener 256 includes a tool socket 106 that is shaped to accept a surgical instrument tool 150. The surgical instrument 150 may be used to assemble and dissemble to components 136, 218.

In the illustrative embodiment, the thread pitch and lead of the section 290 matches the thread pitch and lead of the section 294 so that one rotation of the fastener 256 in either direction results in the same travel axially for the sections 290, 294. Further, the section 290 has a diameter 302 that is greater than a diameter 82 of the first passageway 70 of the tibial tray component 14 (or femoral component 12). Accordingly, the section 290 of the fastener 256 may positioned in the second passageway 72 of the tibial tray component 14 but does not pass beyond the rim surface 74 into the first passageway 70.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic modular knee prosthesis system comprising:
   a femoral stem component adapted to be implanted into a surgically-prepared patient's femur, the femoral stem component including (i) a first end, (ii) an elongated body extending from the first end, (iii) a second end opposite the first end, and (iv) a threaded bore defined in the first end,
   a femoral component including (i) an outer bearing surface having a pair of condyle surfaces sized to articulate with a tibial bearing, wherein the pair of condyle surfaces are spaced apart from one another thereby defining an intercondylar notch therebetween, (ii) a distal opening defined in the intercondylar notch, (iii) an inner bone-engaging surface positioned opposite the outer bearing surface that is configured to face a femur of a patient, and (iv) an elongated stem-mounting post extending from the inner bone-engaging surface along a longitudinal axis, the post including an outer opening defined in a free end and an inner wall that extends inwardly from the outer opening to the distal opening, wherein (a) the inner wall of the post defines a first passageway extending from the distal opening, a second passageway in the post, and a rim surface at an intersection of the first passageway and the second passageway, (b) the first passageway extends from the distal opening to the rim surface, and the second passageway extends from the rim surface to the outer opening, (c) the second passageway includes a plurality of internal threads, and (d) the second passageway of the femoral component has a diameter larger than a diameter of the first passageway,
   a fastener having an elongated shaft including (i) a first axial section having a first plurality of threads sized to engage with the plurality of internal threads of the second passageway of the post of the femoral component, and (ii) a second axial section positioned opposite the first axial section, the second axial section having a second plurality of threads sized to engage with the threaded bore of the femoral stem component to secure the femoral stem component to the femoral component, and
   a surgical instrument tool having an end sized to be received in the first passageway and configured to engage a distal surface of the first axial section of the fastener to selectively rotate the fastener and decouple the femoral stem component from the femoral component,
   wherein the first axial section of the fastener has a diameter larger than a diameter of the second axial section of the fastener and a diameter of the first passageway of the post, such that the first axial section of the fastener does not pass beyond the rim surface and into the first passageway when the first axial section of the fastener is positioned in the second passageway, and
   wherein (i) the first plurality of threads of the first axial section has a first thread pitch and a first lead, (ii) the second plurality of threads of the second axial section has a second thread pitch that is same as the first thread pitch and a second lead that is the same as the first lead, and (iii) the first plurality of threads twist in a same direction as the second plurality of threads.

2. The orthopaedic modular knee prosthesis system of claim 1, wherein the first plurality of threads and the second plurality of threads are one of right-handed threads and left-handed threads.

3. The orthopaedic modular knee prosthesis system of claim 1, wherein rotation of the fastener in a first direction causes the fastener to move axially away from the femoral component within the second passageway of the femoral component.

\* \* \* \* \*